United States Patent
Takada et al.

(10) Patent No.: US 9,340,709 B2
(45) Date of Patent: *May 17, 2016

(54) SUPPORT FILM FOR TAPE AND TAPE

(75) Inventors: Yasunori Takada, Tsukuba (JP); Takito Shima, Tsukuba (JP); Tetsurou Tateishi, Tsukuba (JP); Tsuguki Nishihara, Saitama (JP); Chiaki Yoshida, Oura-gun (JP); Atsushi Matsushima, Kitakatsushika-gun (JP); Tsuyoshi Takamiya, Ogori (JP)

(73) Assignees: HISAMITSU PHARMACEUTICAL CO., INC., Saga (JP); TOPPAN PRINTING CO., LTD., Tokyo (JP); MARUTO SANGYO CO., LTD., Fukuoka (JP)

(*) Notice: Subject to any disclaimer, the term of this patent is extended or adjusted under 35 U.S.C. 154(b) by 457 days.

This patent is subject to a terminal disclaimer.

(21) Appl. No.: 13/812,751

(22) PCT Filed: Jun. 15, 2011

(86) PCT No.: PCT/JP2011/063668
§ 371 (c)(1),
(2), (4) Date: Apr. 5, 2013

(87) PCT Pub. No.: WO2012/014587
PCT Pub. Date: Feb. 2, 2012

(65) Prior Publication Data
US 2013/0209799 A1    Aug. 15, 2013

(30) Foreign Application Priority Data

Jul. 29, 2010  (JP) .................................. 2010-171208

(51) Int. Cl.
*C09J 7/02* (2006.01)
*B32B 27/40* (2006.01)
(Continued)

(52) U.S. Cl.
CPC ............... *C09J 7/0296* (2013.01); *A61L 15/18* (2013.01); *A61L 15/26* (2013.01); *A61L 15/58* (2013.01);
(Continued)

(58) Field of Classification Search
CPC .......... C09J 7/02; C09J 7/0282; C09J 7/0296; C09J 2475/006; C09J 2429/001; A61L 15/18; A61L 15/26; A61L 15/58; A61L 2420/08; C08L 29/04; C08L 75/04; Y10T 428/2848; Y10T 428/31573
USPC ............................................... 428/354, 424.2
See application file for complete search history.

(56) References Cited

U.S. PATENT DOCUMENTS 3,549,452 A    12/1970   Walsh
4,444,819 A *  4/1984   Maruta et al. .................. 503/209
(Continued)

FOREIGN PATENT DOCUMENTS

CN    101454416 A    6/2009
CN    103097130 A    5/2013
(Continued)

OTHER PUBLICATIONS

First Office Action issued May 8, 2014 in Chinese Patent Application No. 201180036480.1 with English translation.
(Continued)

*Primary Examiner* — Thao T Tran
(74) *Attorney, Agent, or Firm* — Sughrue Mion, PLLC

(57) ABSTRACT

A support film for tape which is used for a tape, the support film for tape includes: a film-shaped support formed of polyurethane; and a barrier layer which includes a water-soluble polymer compound and montmorillonite and is formed on one surface of the support. The support film for tape has a percentage content of the montmorillonite in the barrier layer is equal to or more than 2 percent by weight and equal to or less than 22 percent by weight.

4 Claims, 7 Drawing Sheets

(51) Int. Cl.

| | | |
|---|---|---|
| *A61L 15/18* | (2006.01) | |
| *A61L 15/26* | (2006.01) | |
| *A61L 15/58* | (2006.01) | |

(52) U.S. Cl.
CPC ........ *C09J 7/02* (2013.01); *C09J 7/0282* (2013.01); *A61L 2420/08* (2013.01); *C09J 2429/001* (2013.01); *C09J 2475/006* (2013.01); *Y10T 428/2848* (2015.01); *Y10T 428/31573* (2015.04)

(56) References Cited

U.S. PATENT DOCUMENTS

| | | | |
|---|---|---|---|
| 4,875,473 A | 10/1989 | Alvarez | |
| 5,613,958 A | 3/1997 | Kochinke et al. | |
| 5,846,214 A | 12/1998 | Makuuchi et al. | |
| 5,912,204 A * | 6/1999 | Yamada et al. | 503/200 |
| 5,993,961 A | 11/1999 | Ugolick et al. | |
| 7,063,859 B1 | 6/2006 | Kanios et al. | |
| 2002/0055579 A1 | 5/2002 | Oshita et al. | |
| 2005/0196607 A1 * | 9/2005 | Shih et al. | 428/354 |
| 2006/0034905 A1 | 2/2006 | Singh et al. | |
| 2007/0259029 A1 | 11/2007 | McEntire et al. | |
| 2009/0029854 A1 * | 1/2009 | Maruyama et al. | 503/214 |
| 2009/0148640 A1 * | 6/2009 | Yoshida et al. | 428/36.6 |
| 2013/0144226 A1 * | 6/2013 | Takada et al. | 604/307 |
| 2013/0183522 A1 * | 7/2013 | Takada et al. | 428/354 |
| 2013/0184663 A1 * | 7/2013 | Takada et al. | 604/307 |
| 2014/0329063 A1 * | 11/2014 | Shinoda et al. | 428/201 |

FOREIGN PATENT DOCUMENTS

| | | | |
|---|---|---|---|
| CN | 103140351 A | 6/2013 | |
| EP | 0164594 A2 | 12/1985 | |
| GB | 2452086 A | 2/2009 | |
| GB | 2457294 A | 8/2009 | |
| JP | 55-126818 U | 9/1980 | |
| JP | 08-127531 A | 5/1996 | |
| JP | 8-127531 A | 5/1996 | |
| JP | 09-262249 A | 10/1997 | |
| JP | 9-262249 A | 10/1997 | |
| JP | 2003-93434 A | 4/2003 | |
| JP | 2003-136645 A | 5/2003 | |
| JP | 2006-16382 A | 1/2006 | |
| JP | 2008-126631 A | 6/2008 | |
| JP | 2009-173626 A | 8/2009 | |
| JP | 2009-249298 A | 10/2009 | |
| JP | 2009-536647 A | 10/2009 | |
| TW | 200803923 | 1/2008 | |
| WO | 93/11938 A1 | 6/1993 | |
| WO | 96/08369 A1 | 3/1996 | |
| WO | 00/31201 A2 | 6/2000 | |
| WO | 2005/105060 A1 | 11/2005 | |
| WO | 2007/023791 A1 | 3/2007 | |
| WO | 2009/027648 A1 | 3/2009 | |
| WO | 2012/014585 A1 | 2/2012 | |
| WO | 2012/014587 A1 | 2/2012 | |

OTHER PUBLICATIONS

Extended European Search Report issued Nov. 12, 2013 in European Patent Application No. 11812180.5.
International Search Report for PCT/JP2011/063668 dated Sep. 20, 2011.
International Search Report issued Apr. 2, 2013 in International Application No. PCT/JP2013/051284.
The First Office Action issued Mar. 20, 2015 in Chinese Patent Application No. 201380006230.2 with translation.
"Polyvinyl Alcohol", XP002711439, Retrieved from the Internet: URL: http://www.kremer-pigmente.com/niedia/files_public/67700-67790e.pdf [retrieved on Aug. 19, 2013].
International Search Report dated Sep. 20, 2011 from the International Bureau in counterpart International Application No. PCT/JP2011/063656.
Communication dated Apr. 17, 2013 from the European Patent Office in counterpart application No. 11812178.9.
Communication dated Mar. 27, 2014 from the State Intellectual Property Office of the P.R.C. in counterpart application No. 201180036478.4.
Communication dated Apr. 8, 2015 from the U.S. Patent and Trademark Office in counterpart U.S. Appl. No. 13/812,797.
Communication dated Jul. 28, 2015 from the U.S. Patent and Trademark Office in counterpart U.S. Appl. No. 13/812,797.
International Search Report dated Aug. 16, 2011 from the International Bureau in counterpart International Application No. PCT/JP2011/063666.
Communication dated Jul. 12, 2013 from the European Patent Office in counterpart application No. 11812179.7.
Communication dated Feb. 20, 2014 from the European Patent Office in counterpart application No. 11812179.7.
Communication dated Dec. 4, 2014 from the U.S. Patent and Trademark Office in counterpart U.S. Appl. No. 13/812,788.
International Search Report dated Aug. 16, 2011 from the International Bureau in counterpart International Application No. PCT/JP2011/063684.
Communication dated Aug. 29, 2013 from the European Patent Office in counterpart application No. 11812182.1.
Communication dated Apr. 17, 2015 from the Taiwanese Intellectual Property Office in counterpart application No. 100120864.
International Search Report issued Sep. 20, 2011 in International Application No. PCT/JP2011/063668.
Extended European Search Report issued Nov. 12, 2013 in European Application No. 11812180.5.
First Office Action issued May 8, 2014 in Chinese Patent Application No. 201180036480.1 with translation.
Wang Duoren, Green Chemical Assistant, pp. 194 to 195, the Science and Technology Literature Press, Jan. 2006. ISBN 7-5023-5201-5.
Communication dated Dec. 15, 2015 from the State Intellectual Property Office of the P.R.C. in counterpart application No. 201180036478.4.

* cited by examiner

SUPPORT FILM FOR TAPE AND TAPE

CROSS REFERENCE TO RELATED APPLICATIONS

This application is a National Stage of International Application No. PCT/JP2011/063668 filed on Jun. 15, 2011, which claims priority from Japanese Patent Application No. 2010-171208, filed on Jul. 29, 2010, the contents of all of which are incorporated herein by reference in their entirety.

BACKGROUND OF THE INVENTION

1. Field of the Invention

The present invention relates to a support film for tape, and particularly a support film for tape having barrier properties, and a tape using the same.

Priority is claimed on Japanese Patent Application No. 2010-171208, filed Jul. 29, 2010, the content of which is incorporated herein by reference.

2. Description of Related Art

A tape on which an adhesive layer is formed on one surface of a sheet-shaped or film-shaped support has been widely used for various purposes such as for medical use or industrial use. In addition to adhesive materials, in some cases a plasticizer and the like are combined to the adhesive layer of the tape. Since there is a concern over a negative effect due to adsorption of the plasticizer depending on materials of a support, it is preferable that at least a surface of the support which comes into contact with the adhesive layer has barrier properties.

A gas barrier film disclosed in Patent Document 1 (Japanese Unexamined Patent Application, First Publication No. 2003-136645) has been used as a film material having barrier properties. In this gas barrier film, a barrier coating film is formed by applying a barrier coating material which is obtained by mixing montmorillonite, which is a layered inorganic compound, and a water-soluble polymer compound on one surface of a plastic base film.

In addition, Patent Document 2 (Japanese Unexamined Patent Application, First Publication No. H08-127531) discloses a film-shaped support for percutaneously administered medicine including a barrier film formed of polyethylene terephthalate (PET) and the like. Patent Document 3 (Japanese Unexamined Patent Application, First Publication No. 2009-249298) discloses a film-shaped support for a patch having barrier properties by providing a vapor-deposited layer formed of aluminum and the like. Patent Document 4 (Japanese Unexamined Patent Application, First Publication No. 2009-173626) discloses a support for a patch which is obtained by laminating an elastic base film layer and a polyester resin film layer which includes a groove, the width of which changes according to elongation of the base film.

On the other hand, since the tape is attached to an object in a state with increased length and area than an initial state due to elongation, in many cases, it is preferable that the support used for the tape have excellent flexibility.

A gas barrier film disclosed in Patent Document 1 is conceived to be used mainly for packaging materials of food products, electronic components, and the like, and as materials of a base film, a biaxially-drawn polyester film, a polypropylene film and the like are disclosed; however, since it is not certain that these materials have high flexibility, the films may not reliably have a preferable configuration as they are, as a support film for tape which is sometimes elongated when attached.

Herein, the inventors found the following problems when configuring a support film for tape by performing selection and application of a material with further excellent flexibility as a support.

That is, it is possible to prepare a support film for tape using a support formed of a material with excellent flexibility; however, if the support film for tape is elongated in order to be attached to an object or after being attached thereto, a barrier layer cannot sufficiently respond to shape change of the support due to the elongation, and cracks or the like are generated on the barrier layer, in some cases.

If cracks or the like are generated on the barrier layer, barrier properties of the barrier layer are degraded, and if the cracks or the like pass through in a thickness direction of the barrier layer, the barrier properties are lost. As a result, there is a problem with a case in which the barrier layer does not realize an expected performance in use and the negative effect to the support due to the plasticizer described above cannot be sufficiently suppressed.

On the other hand, as disclosed in Patent Document 2, in a configuration including a barrier film formed of PET and the like, there is a problem in that flexibility of the support is not sufficiently realized due to PET and the like, which have low flexibility.

SUMMARY OF THE INVENTION

The present invention has been made to address the aforementioned problems, and aims at providing a support film for tape and a tape which successfully maintain barrier properties even with elongation.

A first aspect of the present invention is to provide a support film for tape which is used for a tape, the support film for tape including: a film-shaped support formed of polyurethane; and a barrier layer which includes a water-soluble polymer compound and montmorillonite and is formed on one surface of the support, wherein a percentage content of the montmorillonite in the barrier layer is equal to or more than 2 percent by weight and equal to or less than 22 percent by weight.

In the support film for tape of the present invention it is desirable that the water-soluble polymer compound be polyvinyl alcohol.

A tape as a second aspect of the present invention includes the support film for tape of the present invention; and an adhesive layer which is formed on the barrier layer on the opposite to the support and includes a plasticizer, and a percentage content of the montmorillonite in the barrier layer is a value so that the barrier layer realizes barrier properties to sufficiently suppress transition of the plasticizer to the support, in any of a case of non-elongation of the support and a case of an elongation rate of the support of 20 percent.

According to the support film for tape and the tape of the present invention, it is possible to successfully maintain barrier properties even when elongated in order to be attached to an object or after being attached thereto.

DETAILED DESCRIPTION OF THE INVENTION

Hereinafter, a tape of an embodiment of the present invention will be described referring to FIGS. 1 to 15. The tape of the embodiment is configured to include a support film for tape (hereinafter, simply referred to as "support film") of the present invention, and the tape can be used as an adhesive tape or the like in various fields such as for industrial use, packaging, protecting, labeling, masking, hygienic materials such as a diaper, medical use such as an adhesive patch or percutaneously administered medicine, make-up, and household use.

In addition, the following are exemplified as representative detailed examples. An adhesive tape for sealing a packaging material is used as a packaging. As the adhesive tape is capable of being elongated, even in a case of applying a force due to shipping or the like in a state of being packaged, the tape is not cut or the packaging material is not damaged. In addition, since it is possible to maintain excellent barrier properties in a state of being elongated, an exterior portion is not contaminated when shipping or the like. For medical use, in a case of attaching to a human body or an animal, it is possible to respond to according to elongation associated with movement of a human body or the like, and unexpected peel-off is hardly generated. In addition, since it is possible to maintain excellent barrier properties in a state of being elongated, it is possible to obtain excellent performances for medical use without leakage of an active ingredient such as a plasticizer or the like, to the external portion.

Figure 1:
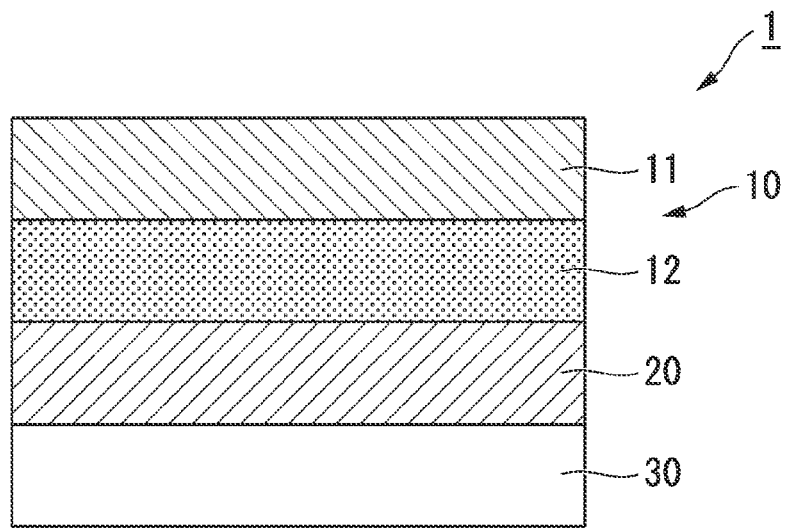
FIG. 1 is a cross-sectional view of a tape of an embodiment of the present invention in a thickness direction.

FIG. 1 is a cross-sectional view of a tape 1 of the embodiment in a thickness direction. The tape 1 includes a support film 10, an adhesive layer 20 formed on one surface of the support film 10, and a peel-off member 30 which covers the adhesive layer.

The support film 10 includes a support 11 which includes polyurethane and is formed in a film shape, and a barrier layer 12 which is formed on one surface of the support 11.

The support 11 has flexibility and can be elongated by a predetermined maximum elongation rate increasing equal to or more than 10 percent (%) dimensionally. A detailed value of the maximum elongation rate may be suitably set based on the purpose of the tape 1. In the embodiment, the polyurethane which forms the support 11 is not particularly limited, and polyurethane used in a polyurethane film of the related art can be used, and the polyurethane can be suitably selected depending on the purpose. For example, polyether-based polyurethane, polyester-based polyurethane, polycarbonate-based polyurethane or the like may be used. To provide water resistance, polyether-based polyurethane or polycarbonate-based polyurethane is preferable.

In addition, it is not particularly limited to a type of isocyanate forming a urethane bond, a yellowing type, or a non-yellowing type, and it is suitably selected according to the purpose, storing period or method of usage, types of used plasticizer and the like.

A thickness of the support 11 is 10 micrometers (μm) to 200 μm, and is preferably equal to or more than 15 μm and equal to or less than 100 μm. When the thickness is less than 10 μm, it is difficult to handle as it is too thin, and when the thickness is more than 200 μm, flexibility is reduced such that the original flexibility is not sufficiently exhibited.

The support 11 can include a film called a release film having a peel-off property. When the thickness of the support 11 is thin, since the support is elongated in a step of applying the barrier layer 12, if manufacturing in a state where the release film and the support (for example, polyurethane as the support) are laminated, it is possible to easily process while suppressing the elongation. In addition, since rigidity of the tape is reinforced by the release film after processing the support 11 on the tape, handleability of the tape is improved. The release film can be adhered to the tape to an object and peeled from the support, such that the support 11 after peeling off exhibits original flexibility.

The material of the release film is not particularly limited; however, generally, a material which can be peeled off without performing elongation or contraction, such as a silicon-treated PET film, a polyolefin film having an excellent peel-off property, an aggregate such as paper or polyethylene, or the like can be used.

The barrier layer 12 is formed to include montmorillonite, which is a layered inorganic compound, and polyvinyl alcohol (PVA), which is a water-soluble polymer compound.

Mineralogically, montmorillonite is a dioctahedral type water-bearing layered silicate mineral and is ideally expressed by the following equation.

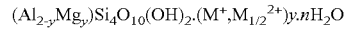

Herein, y=0.2 to 0.6, M: exchangeable cation such as Na, K, Ca, Mg, or H, n: amount of interlayer water.

A crystal structure of montmorillonite forms a layered structure which includes three layers formed of two tetrahedral sheets and one octahedral sheet as a base. A cation of the tetrahedral sheets is only Si, and a cation, Al of the octahedral sheet is substituted for a part of Mg. Accordingly, a unit crystal layer takes on a negative electric charge, and cations such as $Na^+$, $K^+$, $Ca^{2+}$, $Mg^{2+}$, $H^+$, and the like enter and compensate between crystal layers so as to balance with the negative electric charge. In the present invention, types of the cation can be used with no particular limitations.

The barrier layer 12 can be formed by applying a barrier coating material obtained by adding and adjusting lower alcohol with a gravure coating method or a roll coating method, after the montmorillonite is added to and dispersed in a water solution obtained by melting PVA in water. If necessary, an anchor coating layer may be formed on the support 11 and the barrier layer 12 may be formed on the anchor coating layer. In the same manner, the barrier layer 12 may be formed after being subjected to a surface treatment on the support 11. As the surface treatment, a corona discharge treatment or a plasma discharge treatment is preferable. From the above, the corona discharge treatment is more preferable from a viewpoint of general versatility or handleability.

A percentage content of the montmorillonite of the barrier layer 12 is in a range of equal to or more than 2 weight percent (wt %) and equal to or less than 22 wt %. A detailed description will be described later; however, if the percentage content is less than 2 wt %, it is difficult to secure a sufficient barrier property. On the other hand, if the percentage content exceeds 22 wt %, an effect caused by the montmorillonite on the physical property of the barrier layer 12 becomes too much, and as a result, sufficient responding to shape change of the support due to the elongation cannot be performed, and cracks or the like are easily generated.

In addition, when the tape 1 is used in an environment to be placed in water for a long time in a state of being attached to an object, for example, if adhesiveness of the support 11 and the barrier layer 12 is not sufficient, the support 11 is peeled off from the barrier layer 12 and separated from the adhesive layer 20, in some cases. The PVA is a polymer compound which is obtained by saponification of polyvinyl acetate (alkaline hydrolysis treatment) and includes a hydroxyl group; however, in the support film 10 of the embodiment, in order to maintain excellent adhesiveness of the barrier layer 12 and the support 11 to prevent the situation described above, a degree of saponification of PVA is in a range equal to or more than 70% and equal to or less than 95.5%. A detailed description thereof will be also described later; however, if the degree of saponification exceeds 95.5%, the adhesiveness with the support 11 is degraded, and if the degree of saponification is less than 70%, the barrier layer 12 becomes easily melted in water, and as a result, water resistance of the support film 10 and the tape 1 is degraded. Accordingly, when used for industrial applications, packaging, or protecting, it is assumed to be affected by rain outside, and when used for hygienic materials such as a diaper, medical use such as an adhesive patch or percutaneously administered medicine, make-up, or household use, it is assumed to affected by sweat or water when using water in daily life.

The adhesive layer 20 is configured by mixing plasticizer with a base material having an adhesive property and is formed by applying or the like on the barrier layer 12 and a surface opposite to the support 11.

An adhesive used in the adhesive layer 20 is not particularly limited, and a rubber-based polymer such as natural rubber, synthetic isoprene rubber, reclaimed rubber, styrene-butadiene rubber (SBR), styrene-isoprene-styrene block copolymer (SIS), styrene-butadiene-styrene block copolymer (SBS), polyisobutylene, SEBS, SEPS, or the like, acrylic polymers such as a copolymer of (meth) acrylic acid ester containing (meth) acrylic acid ester as a main monomer, silicon-based polymers such as silicon rubber, silicon resin, dimethyl siloxane, diphenyl siloxane, and the like, and various polyvinyl ether-based, polyvinyl ester-based, EVA-based, polyester-based materials can be used.

The plasticizer is not particularly limited, and various plasticizers such as petroleum-based oil (paraffinic process oil, naphthenic process oil, or aromatic process oil), dibasic acid esters (dibutyl phthalate, or dioctyl phthalate), liquid rubbers (polybutene, liquid isoprene, or liquid polyisobutylene), vegetable-based oils (castor oil or tall oil) liquid fatty acid esters (isopropyl myristate, hexyl laurate, diethyl sebacate, or diisopropyl sebacate), triacetin, sorbitan fatty acid esters, sucrose fatty acid esters, glycerin fatty acid esters, and surfactants can be used.

Further, for improving adhesiveness, various tackifiers can be mixed. For example, rosin resins such as rosin, modified rosin, or rosin ester, terpene resins such as terpene resin, aromatic modified terpene resin, hydrogenated terpene resin, or terpene phenol resin, petroleum resin such as aliphatic petroleum resins, aromatic petroleum resins, copolymer petroleum resin, hydrogenated petroleum resin, or DCPD-based petroleum resin, styrene resins, substituted styrene resins, xylene resin, phenol resin, chroman-indene resin or the like can be used.

In addition, depending on the purpose of the tape, antioxidants, fillers, cross-linking agents, ultraviolet absorbers, colorants, flame retardants, conductive agents, foaming agents, or the like may be added.

In the tape 1 of the embodiment, by suitably setting the percentage content of montmorillonite of the barrier layer 12 in the range described above while considering the types of plasticizers, transition of the plasticizer to the support 11 from the barrier layer 12 is suitably suppressed.

In general, polyurethane configuring the support 11 is easily adsorbed onto the plasticizer, and in this case, transformation or the like of the support 11 due to the transition of the plasticizer to the support 11 becomes a problem; however, in the tape 1, not only at the time of non-elongation of the support 11, but even at the time of elongation with the elongation rate of 20% (which indicates an increase of length by 20% after the elongation), the barrier property of the barrier layer 12 is suitably maintained. As a result, not only at the time of storage before the use, but also at the time of being used by being attached to an object, it is possible to suitably prevent the problem due to the plasticizer. In addition, the percentage content of the montmorillonite can be easily set in detail by a preliminary experiment or the like using the plasticizer to be used. A relationship between the barrier property with respect to a part of the plasticizer and the percentage content of montmorillonite will be described later.

The peel-off member 30 is a member to protect an adhesive surface of the adhesive layer 20 until the adhesion to an object, and various types of well-known release paper can be suitably used. In addition, when the tape 1 is rolled up on a core, the peel-off member 30 may not be prepared.

Next, a test and a result thereof performed for evaluating a suitable range of the percentage content of the montmorillonite (hereinafter, referred to as "MN", in some cases) of the barrier layer 12 and a suitable range of the degree of saponification of the PVA will be described.

Experiment 1

Evaluation of Relationship Between Barrier Property and Percentage Content of MN at the Time of Elongation: Evaluation with Swelling of Support as Index 1-1 Preparation of Sample As a support, a material prepared by polyether-based polyurethane having a thickness of 20 μm was used. A barrier layer was formed by uniformly applying 1.0 g/m² of a barrier coating material which was obtained by mixing MN and PVA (with a degree of saponification of 80%) on one surface of the support. By setting this as a basic configuration, 8 stages of the percentage content of MN of the barrier layer were 1 wt %, 2 wt %, 10 wt %, 18 wt %, 22 wt %, 25 wt %, 30 wt %, and 37 wt %, and 8 types of samples of support films were prepared.

1-2 Experiment Procedure

Figure 2:
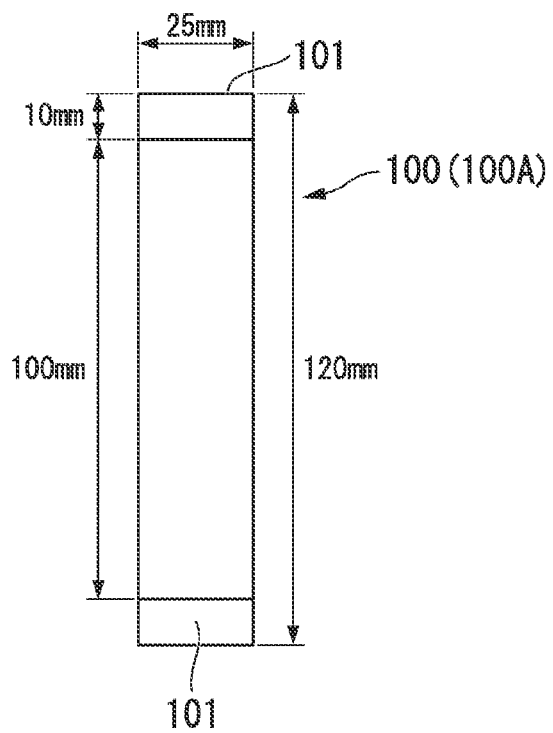
FIG. 2 is a view showing a procedure of an experiment for checking for a suitable range of a percentage content of montmorillonite in a barrier layer.

The prepared 8 types of samples 100 were cut to be a size of 25 millimeters (mm)×120 mm as shown in FIG. 2, and in order to perform easy operation with a tensile tester, a sheet 101 prepared by polyethylene terephthalate (PET) having a thickness of 50 μm was attached to both surfaces of both ends in a longitudinal direction with double-sided tape and an evaluation piece 100A was prepared. A dimension of the evaluation piece 100A of the sheet 101 in the longitudinal direction was 10 mm, and in each evaluation piece 100A, a length of a portion which was not covered with the sheet 101 in the longitudinal direction was 100 mm.

Figure 3:
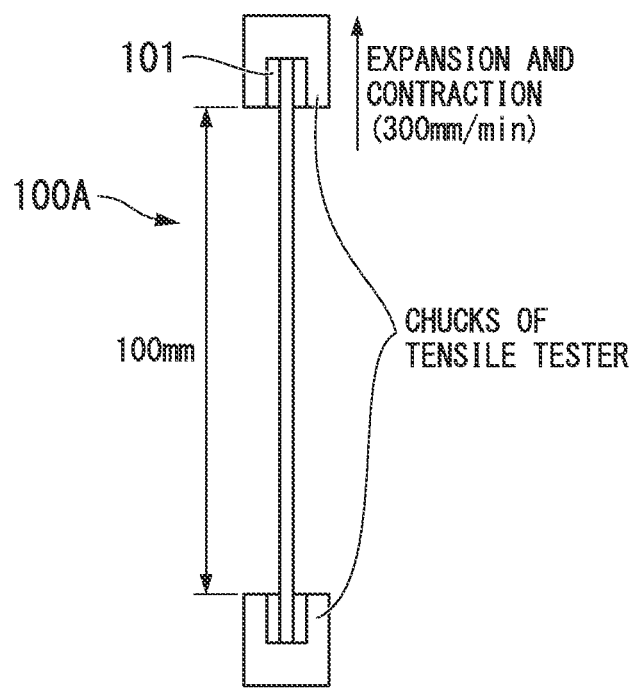
FIG. 3 is a view showing a procedure of the same experiment.

Both ends of the evaluation piece 100A reinforced by the sheet 101 were fixed to the chuck unit of the tensile tester, and as shown in FIG. 3, the portion not covered with the sheet 101 was elongated to reach a predetermined elongation rate with an elongation speed of 300 mm per minute (mm/min). Five stages of elongation rate were 0%, 5%, 10%, 20%, and 30%.

Figure 4:
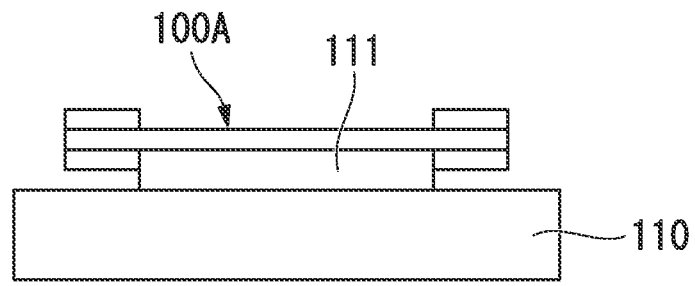
FIG. 4 is a view showing a procedure of the same experiment.

After completing the elongation operation, the evaluation piece 100A was taken off from the tensile tester, and as shown in FIG. 4, each evaluation piece 100A was fixed onto a black acrylic plate 110 obtained by attaching a PET sheet 111 obtained by applying silicon on the surface thereof, with a barrier layer to be on the upper side. At that time, the preparation was performed so that as little air as possible entered between the evaluation piece 100A and the PET sheet 111.

Figure 5:
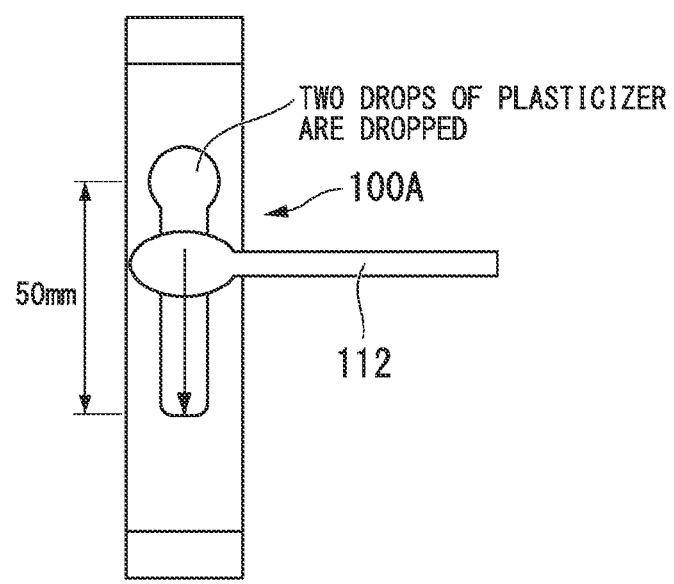
FIG. 5 is a view showing a procedure of the same experiment.
Figure 6:
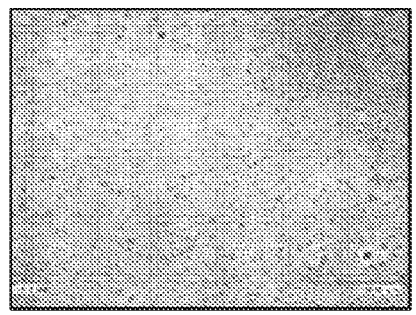
FIG. 6 is an optical micrograph of a barrier layer after performing an elongation operation with an elongation rate of 20% with respect to an evaluated piece with a percentage content of montmorillonite in a barrier layer of 10 wt %.
Figure 7:
FIG. 7 is an optical micrograph of a barrier layer after performing an elongation operation with an elongation rate of 20% with respect to an evaluated piece with a percentage content of montmorillonite in a barrier layer of 18 wt %.
Figure 8:
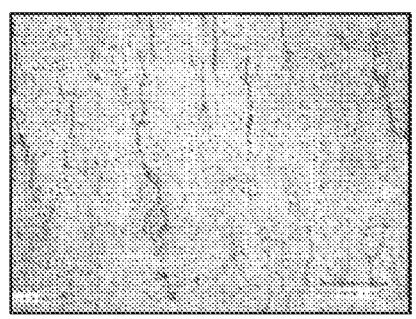
FIG. 8 is an optical micrograph of a barrier layer after performing an elongation operation with an elongation rate of 20% with respect to an evaluated piece with a percentage content of montmorillonite in a barrier layer of 25 wt %.
Figure 9:
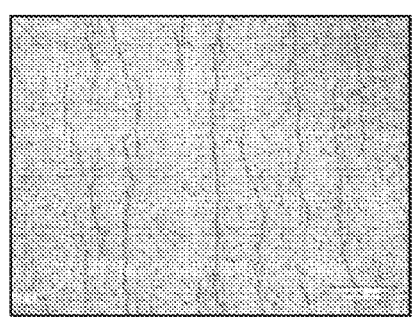
FIG. 9 is an optical micrograph of a barrier layer after performing an elongation operation with an elongation rate of 20% with respect to an evaluated piece with a percentage content of montmorillonite in a barrier layer of 30 wt %.

After attaching to the acrylic plate 110, as shown in FIG. 5, two drops (about 0.08 grams) of plasticizers were put on each evaluation piece 100 by a dropper, and the evaluation piece was expanded to have a length of 50 mm by using a cotton swab 112. As plasticizers, four types of isopropyl myristate (IPM), triacetin (TA), glyceryl monoisostearate (MGIS), and sorbitan monooleate (SMO) were used. After being left for 30 minutes at room temperature, the plasticizers were wiped off and a degree of swelling of the support was visually evaluated. As an index, wrinkles of the support generated due to the swelling were used (two stages of wrinkles due to swelling were not recognized: Good, and wrinkles due to swelling were recognized: Bad).

The IPM, the TA, and the SMO were evaluated using the evaluation pieces 100A having a percentage content of MN of 1 wt %, 10 wt %, 18 wt %, 22 wt %, 25 wt %, 30 wt %, and 37 wt %, and MGIS was evaluated using the evaluation pieces 100A having a percentage content of MN of 2 wt %, 10 wt %, and 22 wt %.

1-3 Result

The result is shown in Table 1. When the percentage content of MN is equal to or less than 22 wt % with the IPM, TA, and MGIS, the swelling of the support with all elongation rates was not recognized, and transition of the plasticizers was suppressed. On the other hand, with the SMO, the swelling was recognized on the support regardless of the percentage content of MN and the elongation rates, and it was considered that the SMO is not preferable as the plasticizer to be used for a film material of the present invention, in some cases. Solubility parameters (SP value based on Fedors method) of each plasticizer used in the experiment were 8.5 for IPM, 10.2 for TA, 10.76 for MGIS, and 11.76 for SMO, and it was assumed that the plasticizer having a low SP value tended to be preferable.

FIGS. 6 to 9 are optical micrographs of the support film after performing the elongation operations with an elongation rate of 20% with respect to the evaluated pieces with a percentage content of MN of 10 wt %, 18 wt %, 25 wt %, and 30 wt %. In a case of 10 wt % and 18 wt % of the MN, significant changes on the external portion were not recognized; however, in a case of 25 wt % and 30 wt % of the MN, wrinkles due to the swelling were recognized.

TABLE 1

| Sample configuration | | | Evaluation | | | | | | | | | |
|---|---|---|---|---|---|---|---|---|---|---|---|---|
| | Barrier layer formula | | IPM | | | | | TA | | | | |
| | Degree of saponification | Amount of | Elongation rate (%) | | | | | Elongation rate (%) | | | | |
| Support | of PVA % | MN wt % | 0 | 5 | 10 | 20 | 30 | 0 | 5 | 10 | 20 | 30 |
| Ethers 20 μm | 80 | 1 | Good | Good | Good | Good | Good | Good | Good | Good | Good | Good |
| | | 2 | None | None | None | None | None | None | None | None | None | None |
| | | 10 | Good | Good | Good | Good | Good | Good | Good | Good | Good | Good |
| | | 18 | Good | Good | Good | Good | Good | Good | Good | Good | Good | Good |
| | | 22 | Good | Good | Good | Good | Good | Good | Good | Good | Good | Good |
| | | 25 | Good | Good | Bad | Bad | Bad | Good | Bad | Bad | Bad | Bad |
| | | 30 | Good | Bad | Bad | Bad | Bad | Good | Bad | Bad | Bad | Bad |
| | | 37 | Bad | Bad | Bad | Bad | Bad | Bad | Bad | Bad | Bad | Bad |
| Sample configuration | | | Evaluation | | | | | | | | | |
| | Barrier layer formula | | MGIS | | | | | SMO | | | | |
| | Degree of saponification | Amount of | Elongation rate (%) | | | | | Elongation rate (%) | | | | |
| Support | of PVA % | MN wt % | 0 | 5 | 10 | 20 | 30 | 0 | 5 | 10 | 20 | 30 |
| Ethers 20 μm | 80 | 1 | None | None | None | None | None | Bad | Bad | Bad | Bad | Bad |
| | | 2 | Good | Good | Good | Good | Good | None | None | None | None | None |
| | | 10 | Good | Good | Good | Good | Good | Bad | Bad | Bad | Bad | Bad |
| | | 18 | None | None | None | None | None | None | Bad | Bad | Bad | Bad |
| | | 22 | Good | Good | Good | Good | Good | Bad | Bad | Bad | Bad | Bad |

TABLE 1-continued

| | | | | | | | | | | |
|---|---|---|---|---|---|---|---|---|---|---|
| 25 | None | None | None | None | None | Bad | Bad | Bad | Bad | Bad |
| 30 | None | None | None | None | None | Bad | Bad | Bad | Bad | Bad |
| 37 | None | None | None | None | None | Bad | Bad | Bad | Bad | Bad |

Figure 10:
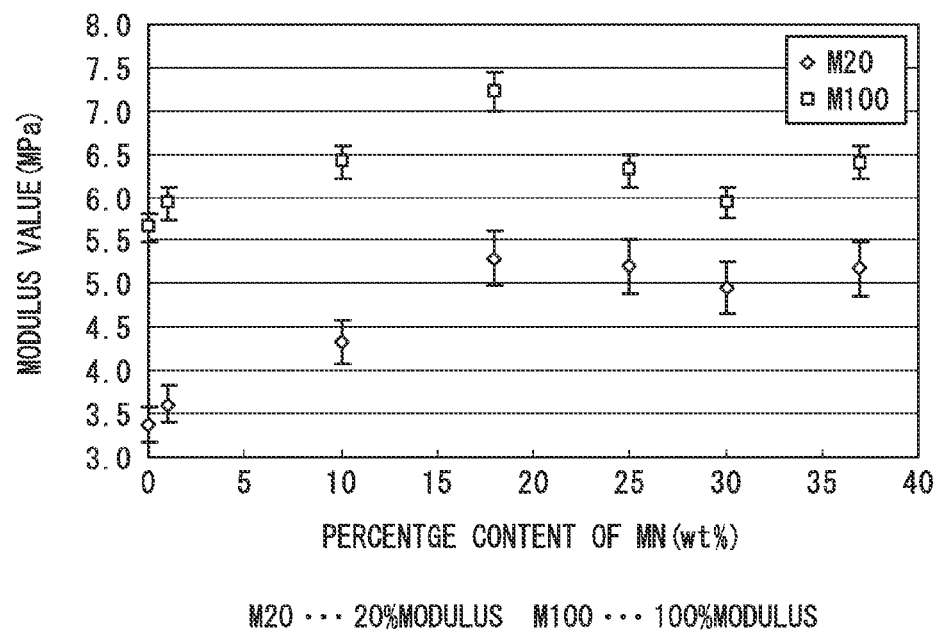
FIG. 10 is a graph showing a relationship between a percentage content of montmorillonite and a modulus value of a support film for tape.

In addition, in each sample, when evaluating modulus after the elongation operation based on a test method of a polyurethane-based thermoplastic elastomer (JIS K 7311), as shown in FIG. 10, the modulus was equal to or less than 8 Mega Pascals (MPa) for all samples, and excellent flexibility was shown. Accordingly, it was determined that the barrier layer did not negatively affect the flexibility of the support film.

Experiment 2

Evaluation of Relationship Between Barrier Property and Percentage Content of MN: Evaluation Using Adhesive Layer Containing Plasticizer 2-1 Preparation of Sample The same material as Experiment 1 was used as a support, and a barrier layer was formed by uniformly applying 1.0 g/m² of a barrier coating material which was obtained by mixing MN and PVA (with a degree of saponification of 80%) on one surface of the support. Nine stages of the percentage content of MN of the barrier layer were 1 wt %, 2 wt %, 4 wt %, 10 wt %, 18 wt %, 22 wt %, 25 wt %, 30 wt %, and 37 wt %, and 9 types of samples of support films were prepared.

In addition, an adhesive layer (applied amount of adhesive layer: 100 g/m²) including a base material and a plasticizer was formed on the barrier layer. Two types of rubber base material and an acrylic base material were used as the base material, and a total of 5 types of adhesive layer materials were prepared by combining each base material with a plurality of types of plasticizers. The adhesive layer was formed on each sample using each an adhesive layer material, and samples of tapes were prepared by covering the adhesive layer with a peel-off member. The combinations of the base material and the plasticizer for each adhesive layer material were as follows (% of the plasticizer indicates the percentage content). Rubber base material (IPM 20%, MGIS 10%, SMO 10%, and SMO 20%) And the acrylic base material (IPM 20%, TA 10%, MGIS 10%, and SMO10%)

2-2 Experiment Procedure a. Stability Test for Non-Elongation Time
A tape sample obtained by cutting to 10 square centimeters was stored at 60° C. for 1 week without performing an elongation operation.

b. Stability Test for Elongation Time
A tape sample obtained by cutting to have a width of 30 mm and a length of 50 mm was stored at 60° C. for three days after removing the peel-off member and performing the elongation operation with an elongation rate of 20% in a length direction once.

In all cases, in each tape sample after storing, in the same manner as Experiment 1, the barrier property was evaluated by the generation of wrinkles of the support. The evaluation of Experiment 2 was set as three stages. Wrinkles due to the swelling were not recognized: Excellent, slight wrinkles due to the swelling were recognized, but did not affect the quality: Good, and wrinkles due to the swelling were recognized and the support could not be used: Bad.

2-3 Experiment Results

The result is shown in Table 2. When the percentage content of the MN is 2 wt %, 10 wt %, and 18 wt %, in any of the non-elongation time and the 20% elongation time, wrinkles were not recognized in the support and the barrier property was excellently maintained.

In addition, for the SMO, which was considered to be not preferable sometimes in Experiment 1, it was determined that the transition of the plasticizers to the support can be sufficiently suppressed by suitably setting the percentage content of MN of the barrier layer or the percentage content of the plasticizers of the adhesive layer.

TABLE 2

| | Rubber based material | | | | | | | |
|---|---|---|---|---|---|---|---|---|
| | IPM 20% | | MGIS 10% | | SMO 10% | | SMO 20% | |
| Amount of MN (wt %) | Non elongation | Elongation rate 20% | Non elongation | Elongation rate 20% | Non elongation | Elongation rate 20% | Non elongation | Elongation rate 20% |
| 1 | Bad | Bad | Bad | Bad | Bad | Bad | Bad | Bad |
| 2 | Excellent | Excellent | Bad | Bad | Bad | Bad | None | None |
| 4 | None | None | Good | Good | Bad | Bad | None | None |
| 10 | Excellent | Excellent | Excellent | Excellent | Good | Good | Bad | Bad |
| 18 | Excellent | Excellent | Excellent | Excellent | Excellent | Excellent | Bad | Bad |
| 22 | Excellent | Excellent | Excellent | Excellent | Excellent | Excellent | None | None |
| 25 | Bad | Bad | None | None | None | None | Bad | Bad |
| 30 | Bad | Bad | None | None | None | None | Bad | Bad |
| 37 | Bad | Bad | None | None | None | None | Bad | Bad |

| | Acrylic base material | | | | | | | |
|---|---|---|---|---|---|---|---|---|
| | IPM 20% | | MGIS 10% | | SMO 10% | | SMO 20% | |
| Amount of MN (wt %) | Non elongation | Elongation rate 20% | Non elongation | Elongation rate 20% | Non elongation | Elongation rate 20% | Non elongation | Elongation rate 20% |
| 1 | Bad | Excellent | Bad | Bad | Bad | Bad | Bad | Bad |
| 2 | Excellent | Good | None | None | Bad | Bad | Bad | Bad |

TABLE 2-continued

| | | | | | | | | |
|---|---|---|---|---|---|---|---|---|
| 4 | Excellent | Excellent | None | None | Good | Good | Bad | Bad |
| 10 | Excellent | Excellent | Bad | Bad | Excellent | Good | Good | Excellent |
| 18 | Excellent | Excellent | Good | Good | Excellent | Excellent | Excellent | Excellent |
| 22 | Excellent | Excellent | Excellent | Excellent | Excellent | Excellent | Excellent | Excellent |
| 25 | None | Bad | None | Good | None | None | None | Bad |
| 30 | Excellent | Bad | Excellent | Good | None | None | Excellent | Bad |
| 37 | Good | Bad | Excellent | Good | None | None | Excellent | Bad |

The results of Experiments 1 and 2 show that, if the percentage content of the MN of the barrier layer 12 is set in a range equal to or more than 2 wt % and equal to or less than 22 wt %, a barrier property for sufficiently suppressing the transition of the plasticizer to the support can be secured in any of the non-elongation time and the 20% elongation time.

Experiment 3

Evaluation of Relationship Between Degree of Saponification of PVA and Adhesiveness of Support-Barrier Layer: Evaluation of Water Resistance Adhesion 3-1 Preparation of Sample A support was prepared in the same manner as Experiment 1, and a degree of saponification of PVA to be used for a barrier layer was four stages of 80%, 90%, 95.5% and 98.5% (complete saponification). A barrier coating material was prepared by mixing the PVA of each degree of saponification and the MN, and was applied to form a barrier layer with the same amount and method as Experiment 1, and a sample 120 of the support film was prepared. The percentage content of the MN of the barrier layer was 10 wt %.

Figure 11:
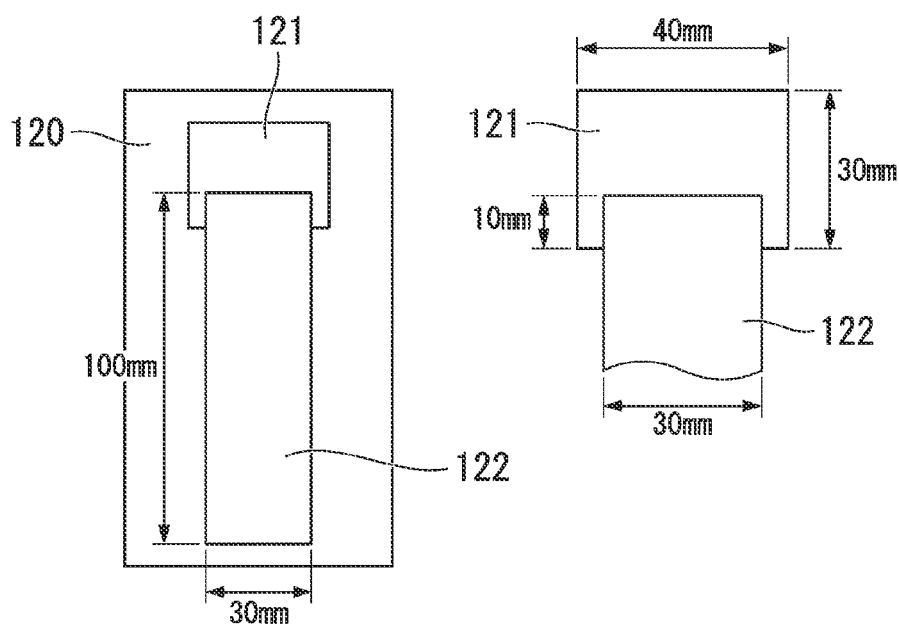
FIG. 11 is a view showing a procedure of an experiment for checking for a relationship between a degree of saponification of a water-soluble polymer compound and an adhesiveness of a support-barrier layer.
Figure 12:
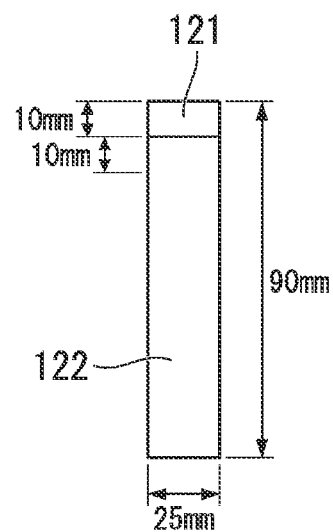
FIG. 12 is a view showing a procedure of the same experiment.
Figure 13:
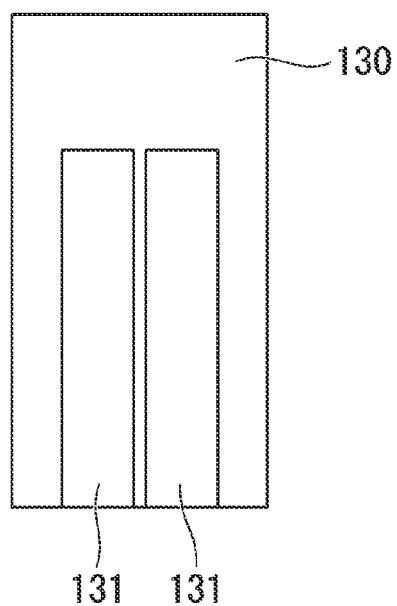
FIG. 13 is a view showing a procedure of the same experiment.
Figure 14:
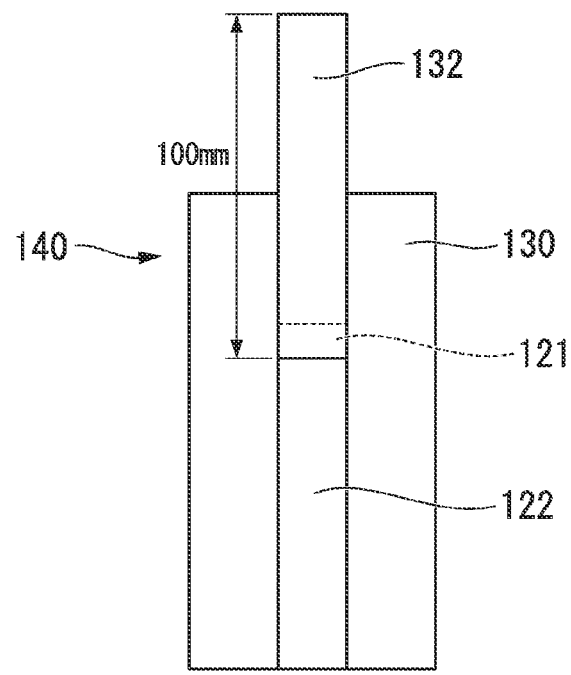
FIG. 14 is a view showing a procedure of the same experiment.
Figure 15:
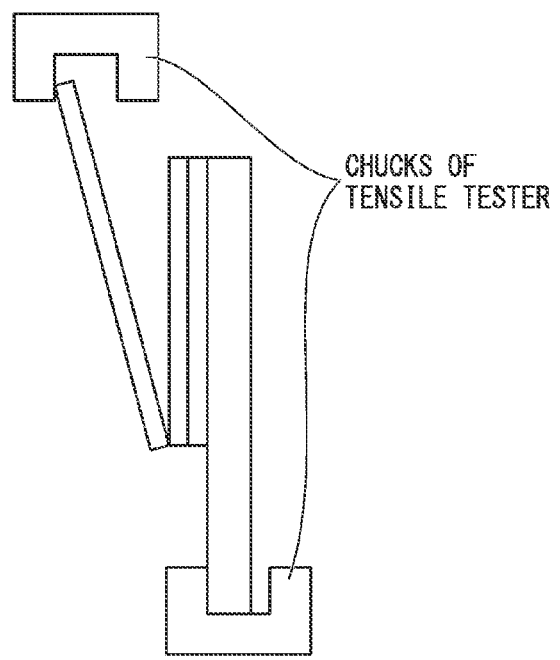
FIG. 15 is a view showing a procedure of the same experiment.

3-2 Experiment Procedure a. After cutting an adhesive tape 122 to 30 mm×100 mm and attaching a PET sheet 121 on which silicon was applied to one end in the longitudinal direction, the adhesive tape was attached to the barrier layer of the sample 120 as shown in FIG. 11.

b. The adhesive tape 122, the PET sheet 121 and the sample 120 were cut to have a size of 25 mm×90 mm as shown in FIG. 12.

c. As shown in FIG. 13, two double-sided tapes 131 having a size of 25 mm 90 mm were attached to be in parallel to each other to an acrylic plate 130, and the support side of the cut adhesive tape 122 and the double-sided tapes 131 were adhered so as to cover two double-sided tapes 131. A part of the double-sided tapes 131 which protruded in a width direction of the adhesive tape 122 was cut off to remove from the acrylic plate 130.

d. A reinforcement tape 132 having a size of 50 mm×100 mm was prepared, and as shown in FIG. 14, the reinforcement tape 132 was attached to the end of the adhesive tape 122 which was not adhered to the sample 120 so as to interpose the PET sheet 121 in the thickness direction, to prepare an evaluation piece 140.

e. The evaluation piece 140 was dipped in water at 40° C. and left for 30 minutes. At that time, the entire adhesive tape 122 was positioned in the water.

f. The evaluation piece 140 was picked up from the water after 30 minutes had passed, and was set in the tensile tester after wiping off the moisture. At that time, as shown in FIG. 15, the acrylic plate 130 was fixed to one chuck, and an end of a side which was not adhered to the PET sheet of the reinforcement tape 132 was fixed to another chuck.

g. The evaluation piece was pulled with a tension rate of 300 mm/min, and the measurement ended at the point of complete peel-off of the adhesive tape 122 from the support. An average value of tension values N of the tensile tester with a range of tension amount from 10 mm to 30 mm was set as a water resistance adhesion. Three evaluation pieces were prepared for a sample and the water resistance adhesion was evaluated.

3-3 Experiment Results

The result is shown in Table 3. With the evaluation piece having the degree of saponification of PVA of equal to or less than 95.5%, the average value of the tension values N was equal to or more than 10 Newtons (N) and excellent water resistance adhesion was shown. With the evaluation piece having the degree of saponification of 98.5%, the water resistance adhesion was significantly degraded. Accordingly, in order to obtain excellent adhesiveness of the support and the barrier layer, it was considered that the degree of saponification of the water-soluble polymer was preferably equal to or less than 95.5%.

TABLE 3

| Degree of saponification | Amount of MN | Water resistance adhesion [N/25 mm width] | | |
|---|---|---|---|---|
| of PVA | (wt %) | n = 1 | n = 2 | n = 3 |
| 80 | 10 | 13.5 | 13.1 | 17.2 |
| 90 | | 10.6 | 10.2 | 10.6 |
| 95.5 | | 14.1 | 13 | 13.5 |
| 98.5 | | 1.9 | 2.6 | 2.1 |

As described above, in the support film of the present invention, by setting the percentage content of MN of the barrier layer to be equal to or more than 2 wt % and equal to or less than 22 wt %, it is possible to suitably maintain the barrier property even with elongation to an elongation rate of 20%. As a result, in any case of the non-elongation time and the elongation to an elongation rate of 20%, it is possible to suitably maintain a barrier property and to form a tape which suitably prevents transition of plasticizers of an adhesive layer to a support.

In addition, by setting a degree of saponification of PVA of the barrier layer to be equal to or more than 70% and equal to or less than 95.5%, it is possible to obtain excellent adhesiveness of the support and the barrier layer, and to configure a support film and a tape which can resist under more varied use conditions.

In addition, as shown in the following Table 4, when the percentage content of MN of the barrier layer was fixed to 10 wt % and several patterns of the degree of saponification of PVA were evaluated, it was determined that there was no significant effect on the barrier property in a range of the degree of saponification equal to or more than 90%.

TABLE 4

| Sample configuration | | | Evaluation | | | | | | | | | |
| --- | --- | --- | --- | --- | --- | --- | --- | --- | --- | --- | --- | --- |
| | Barrier layer formula | | IPM | | | | | TA | | | | |
| | Degree of saponification | Amount of MN | Elongaion rate (%) | | | | | Elongaion rate (%) | | | | |
| Support | of PVA % | wt % | 0 | 5 | 10 | 20 | 30 | 0 | 5 | 10 | 20 | 30 |
| Ethers 20 μm | 90 | 10 | Good | Good | Good | Good | Good | Good | Good | Good | Good | Good |
| | 95.5 | 10 | Good | Good | Good | Good | Good | Good | Good | Good | Good | Good |
| | 98.5 | 10 | Good | Good | Good | Good | Good | Good | Good | Good | Good | Good |

| Sample configuration | | | Evaluation | | | | | | | | | |
| --- | --- | --- | --- | --- | --- | --- | --- | --- | --- | --- | --- | --- |
| | Barrier layer formula | | MGIS | | | | | SMO | | | | |
| | Degree of saponification | Amount of MN | Elongaion rate (%) | | | | | Elongaion rate (%) | | | | |
| Support | of PVA % | wt % | 0 | 5 | 10 | 20 | 30 | 0 | 5 | 10 | 20 | 30 |
| Ethers 20 μm | 90 | 10 | Good | Good | Good | Good | Good | Bad | Bad | Bad | Bad | Bad |
| | 95.5 | 10 | Good | Good | Good | Good | Good | Bad | Bad | Bad | Bad | Bad |
| | 98.5 | 10 | Good | Good | Good | Good | Good | Good | Good | Bad | Bad | Bad |

As described above, the embodiment of the present invention has been described; however, the technique range of the present invention is not limited to the embodiment described above, and it is possible to change combinations of constituent elements of each embodiment, to add and remove various modifications to and from each constituent element in a range not departing from the purpose of the present invention.

For example, it is not essential to set the degree of saponification of PVA to the range described above in the support film and the tape of the present invention. Accordingly, PVA having a value of a degree of saponification out of the range described above or other water-soluble polymers may be used for the barrier layer in a case where the usage environment of a tape is not that severe.

The present invention can be widely used for a tape for various purposes such as for medicine, industrial applications and the like.

What is claimed is:

1. A support film for tape comprising:
   a film-shaped support formed of polyurethane, the film-shaped support being disposed on an outermost surface of the support film, the film-shaped support having a thickness being 10 μm to 200 μm; and
   a barrier layer which includes a water-soluble polymer compound and montmorillonite, and which is formed on one surface of the film-shaped support,
   wherein a percentage content of the montmorillonite in the barrier layer is equal to or more than 2 percent by weight and equal to or less than 22 percent by weight.

2. The support film for tape according to claim 1, wherein the water-soluble polymer compound is polyvinyl alcohol.

3. A tape comprising:
   the support film for tape according to claim 1; and
   an adhesive layer which is formed on the barrier layer on the opposite to the film-shaped support and includes a plasticizer.

4. A tape comprising:
   the support film for tape according to claim 2; and
   an adhesive layer which is formed on the barrier layer on the opposite to the film-shaped support and includes a plasticizer.

* * * * *